United States Patent [19]
Hirota

[11] Patent Number: 6,147,215
[45] Date of Patent: Nov. 14, 2000

[54] PROCESS FOR PRODUCING 1-CHLOROCARBONYL-4-PIPERIDINOPIPERIDINE OR HYDROCHLORIDE THEREOF

[75] Inventor: Hiroshi Hirota, Tokyo, Japan

[73] Assignee: Kabushiki Kaisha Yakult Honsha, Tokyo, Japan

[21] Appl. No.: 09/402,470

[22] PCT Filed: Mar. 31, 1998

[86] PCT No.: PCT/JP98/01465

§ 371 Date: Oct. 12, 1999

§ 102(e) Date: Oct. 12, 1999

[87] PCT Pub. No.: WO98/46568

PCT Pub. Date: Oct. 22, 1998

[30] Foreign Application Priority Data

Apr. 11, 1997 [JP] Japan .................................. 9-093723

[51] Int. Cl.⁷ .................................................. C07D 211/58
[52] U.S. Cl. ................................................................ 546/189
[58] Field of Search ............................................. 546/189

[56] References Cited

U.S. PATENT DOCUMENTS 4,604,463  8/1986  Miyasaka ................................ 544/125

FOREIGN PATENT DOCUMENTS 61-50985  3/1986  Japan .

WO 92/07856  5/1992  WIPO .

OTHER PUBLICATIONS

B. Hermans, et al., J.Med. Chem., vol. 9, pp. 49–52, "4–Substituted Piperidines. III. Reduction of 1–Benzyl–4–Cyano–4–t–Aminopiperidines with Lithium Aluminium Hydride," Jan. 1966.

S. Sawada, et al., Chemi. Pharm. Bull., vol. 39, No. 6, pp. 1446–1454, "Synthesis and Antitumor Activity of 20(S)–Camptothecin Derivatives: carbamate–Linked, Water–Soluble Derivatives of 7–Ethyl–10–Hydroxycomptothecin," 1991.

*Primary Examiner*—Evelyn Mei Huang
*Attorney, Agent, or Firm*—Oblon, Spivak, McClelland, Maier & Neustadt, P.C.

[57] ABSTRACT

The present invention provides a highly safe and easily operable process for producing 1-chlorocarbonyl-4-piperidinopiperidine or hydrochloride thereof in a high yield. Described specifically, the present invention relates to a process for producing 1-clorocarbonyl-4-piperidinopiperidine or hydrochloride thereof, which comprises reacting 4-piperidinopiperidine with a trialkylsilyl halide to obtain a 4-piperidinopiperidinyl trialkylsilyl, reacting it with a carbon dioxide gas to obtain a 4-piperidinopiperidinyl trialkylsilyl carbamate derivative, reacting the derivative with thionyl chloride or the like to obtain 1-chlorocarbonyl-4-piperidinopiperidine hydrochloride and optionally treating it with a strong base.

1 Claim, No Drawings

PROCESS FOR PRODUCING 1-CHLOROCARBONYL-4-PIPERIDINOPIPERIDINE OR HYDROCHLORIDE THEREOF

This application is the national phase of PCT/JP98/01465, filed on Mar. 31, 1998.

TECHNICAL FIELD

The present invention relates to a novel process for producing 1-chlorocarbonyl-4-piperidinopiperidine or hydrochloride thereof, which is an important intermediate as an amide group and is used in the fields of pharmaceuticals and the like.

BACKGROUND OF THE INVENTION

1-Chlorocarbonyl-4-piperidinopiperidine and hydrochloride thereof are important intermediates as the members of amide group and are used widely in the fields of pharmaceuticals and the like.

As an example of processes for producing 1-chlorocarbonyl-4-piperidinopiperidine or hydrochloride thereof, there is a report by S. Sawada (S. Sawada, Chem. Pharm. Bull., 39, 1446(1991)), whose process is characterized by reacting 4-piperidinopiperidine with a phosgene dimer (TCF), removing an unreacted portion of the phosgene dimer to obtain 1-chlorocarbonyl-4-piperidinopiperidine hydrochloride and, if necessary, treating this hydrochloride with an aqueous solution of a weak base such as sodium bicarbonate or potassium carbonate.

However, this process is not suitable for a large scale production of 1-chlorocarbonyl-4-piperidinopiperidine and hydrochloride thereof, as the phosgene dimer is extremely highly toxic and must be treated using special devices in a special operation area and moreover, its transportation is strictly regulated. In addition, this product is precipitated as a hydrochloride in an agar-like form and the unreacted phosgene dimer takes long time to be filtrated out, leading to a high risk in that operators could be exposed to the toxicity of the phosgene dimer. Furthermore, the yield obtained by this process is poor. Because the precipitated hydrochloride is directly dissolved into the aqueous solution and is hydrolyzed under the condition of a weak base of the aqueous solution, every part of the hydrochlorides cannot be converted to 1-chlorocarbonyl-4-piperidinopiperidine.

An object of the present invention is therefore to provide a highly safe and easily operable process for producing 1-chlorocarbonyl-4-piperidinopiperidine or hydrochloride thereof in a high yield.

DISCLOSURE OF THE INVENTION

In view of the forgoing circumstances, the present inventors have conducted an extensive investigation with a view toward attaining the above object. As a result, it has been found that 1-chlorocarbonyl-4-piperidinopiperidine or hydrochloride thereof can be obtained easily and safely in a high yield by trialkylsilylating 4-piperidinopiperidine, reacting the resulting compound with a carbon dioxide gas and then with thionyl chloride or the like and optionally treating with a strong base, leading to the completion of the present invention.

The present invention can be represented by the following reaction scheme:

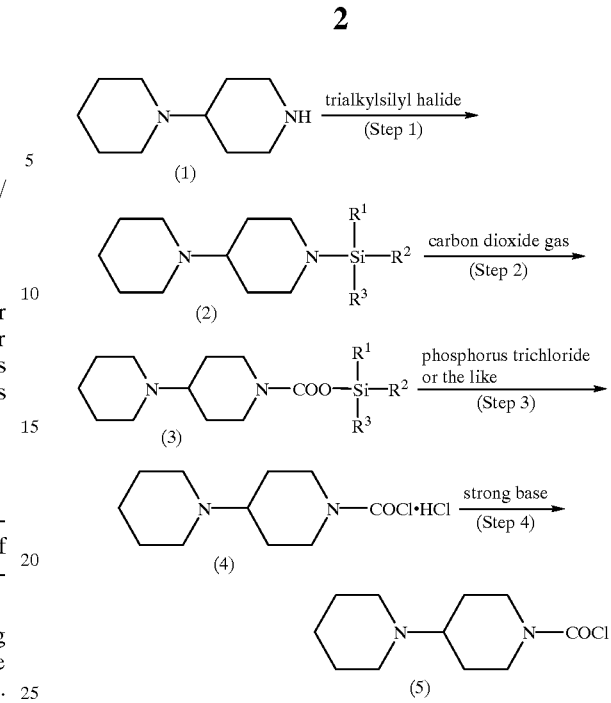

wherein $R^1$, $R^2$ and $R^3$ are the same or different and each represents a linear or branched $C_{1-6}$ alkyl group.

Described specifically, in the present invention, there is thus provided a process for producing 1-chlorocarbonyl-4-piperidinopiperidine hydrochloride represented by the formula (4) or 1-chlorocarbonyl-4-piperidinopiperidine represented by the formula (5), which comprises reacting (step 1) 4-piperidinopiperidine represented by the formula (1) with a trialkylsilyl halide to obtain a 4-piperidinopiperidinyl trialkylsilyl represented by the formula (2), reacting (step 3) the resulting compound with a carbon dioxide gas to form a 4-piperidinopiperidinyl trialkylsilylcarbamate derivative represented by the formula (3), reacting the resulting derivative with one or more substances selected from the group consisting of thionyl chloride, phosphorus trichloride, phosphorus pentachloride, oxalyl chloride and phosphoryl trichloride to obtain 1-chlorocarbonyl-4-piperidinopiperidine hydrochloride represented by the formula (4) and then optionally treating the resulting hydrochloride with a strong base.

Best Modes for Carrying Out the Invention

The process of the present invention will hereinafter be described in the order of steps.

(1) Step 1

The trialkylsilyl halide to be reacted with 4-piperidinopiperidine has a structure in which a silicon atom is bounded by three alkyl groups and one halogen atom. Examples of the alkyl group include linear or branched $C_{1-6}$ alkyl groups. Each of the three alkyl groups may be the same or different. Specific examples include methyl, ethyl, n-propyl, i-propyl, n-butyl, i-butyl, sec-butyl, t-butyl, n-pentyl, i-pentyl, sec-pentyl, t-pentyl and cyclopentyl. In the present invention, $C_{1-4}$ alkyl groups are particularly preferred. Examples of the halogen atom include chlorine, bromine and iodine, with chlorine being particularly preferred.

In a proper solvent such as methylene chloride, benzene or acetonitrile, a trialkylsilyl halide and 4-piperidinopiperidne were dissolved separately. While one of the resulting solutions is stirred as needed, another one is gradually added dropwise thereto at room temperature or lower, whereby they are reacted. Stirring is continued for further 30 minutes to 6 hours to obtain a 4-piperidinopiperidinyl trialkylsilyl (2). It is preferred to effect the reaction, for example, under a nitrogen atmosphere. In addition, it is preferred to add a trialkylsilyl halide in an amount (molar ratio) greater than 4-piperidinopiperidine.

(2) Step 2

While the solution obtained in the step 1 is stirred as needed, a carbon dioxide gas is blown into the solution, whereby a 4-piperidinopiperidinyl trialkylsilyl carbamate derivative (3) is formed. It is preferred that the carbon dioxide gas is blown into the solution in an amount (molar ratio) twice as much as that of 4-piperidinopiperidine at room temperature and atmospheric pressure over 30 minutes to 6 hours.

(3) Step 3

To the solution obtained in the step 2, one or more substances selected from the group consisting of thionyl chloride, phosphorus trichloride, phosphorus pentachloride, phosphoryl trichloride and oxalyl chloride is added dropwise at room temperature or lower. After the completion of the dropwise addition, stirring is continued for about 1 to 48 hours. The reaction mixture is then filtered to remove the remaining 4-piperidinopiperidine hydrochloride, whereby 1-chlorocarbonyl-4-piperidinopiperidine hydrochloride of the present invention is obtained in the filtrate. The reaction at this time is preferably conducted, for example, under a nitrogen atmosphere. It is preferred to add thionyl chloride or the like in an equal amount (molar ratio) to the trialkylsilyl halide. The hydrochloride so obtained is washed with water, dried, concentrated and recrystallized in a manner known per se in the art, whereby a high-purity 1-chlorocarbonyl-4-piperidinopiperidine hydrochloride (4) is obtained.

(4) Step 4

The filtrate obtained in the step 3 is added to an aqueous solution of a strong base. Examples of the strong base usable herein include sodium hydroxide, potassium hydroxide, calcium hydroxide, barium hydroxide, magnesium hydroxide and ammonium hydroxide. No particular limitation is imposed on the concentration of such a strong base, but 0.5 to 50 wt. % is preferred, with 1 to 30 wt. % being particularly preferred. By such a treatment, 1-chlorocarbonyl-4-piperidinopiperidine is obtained in an organic layer. The product so obtained is washed with water, dried, concentrated and recrystallized in a manner known per se in the art, whereby high-purity 1-chlorocarbonyl-4-piperidinopiperidine (5) can be obtained in a high yield. In the present invention, the above-described steps 1 to 4 can be conducted in the reactor of the step 1, which brings about a significant improvement in yield compared with the conventional method.

Alternatively, in the case where preferential synthesis of 1-chlorocarbonyl-4-piperidinopiperidine (in the free form) is intended, it is possible to incorporate a basic substance, such as triethylamine, to use it as a hydrogen chloride scavenger at the step 3.

EXAMPLE

The present invention will hereinafter be described in more detail by Example, but it should however be borne in mind that the present invention is not limited to or by the following Example.

Example 1

Synthesis of 1-chlorocarbonyl-4-piperidinopiperidine (1-5)

In 300 ml of methylene chloride, 20 ml (158 mmol) of trimethylsilyl chloride were dissolved. While the resulting solution was stirred under ice cooling in a nitrogen atmosphere, a solution of 22 g (131 mmol) of 4-piperidinopiperidine (1-1) dissolved in 100 ml of methylene chloride was gradually added dropwise over one hour. The resulting mixture was stirred at room temperature for one hour, whereby a solution containing 4-piperidinopiperidinyl trimethylsilyl (1-2) was obtained. While stirring the resulting solution, 5.9 liter (262 mmol) of a carbon dioxide gas of 1 atomic pressure were blown into the solution over two hours, whereby a solution containing 4-piperidinopiperidinyl trimethylsilyl carbamate derivative (1-3) was obtained. To the resulting solution, 11.5 ml (158 mmol) of thionyl chloride were added dropwise over 10 minutes under ice cooling and nitrogen atmosphere, followed by stirring at room temperature for 18 hours, whereby a solution containing 1-chlorocarbonyl-4-peridinopiperidine hydrochloride (1-4) was obtained. The solution was filtered and 8.8 g (33%) of 4-piperidinopiperidine hydrochloride were recovered as a residue. Under ice cooling, the filtrate was added to 330 ml of a 10% aqueous solution of sodium hydroxide. Then the organic layer obtained by separation was washed with water, dried over anhydrous magnesium sulfate and then concentrated under a low pressure. Isopropyl ether (50 ml) was added to the concentrate to dissolve the latter in the former, followed by cooling at 0° C. for 2 hours. The precipitate was then removed by filtration and the residue was concentrated under reduced pressure. The concentrate so obtained was recrystallized from 50 ml of n-hexane, whereby 15 g of the title compound (1-5) were obtained. The compound so obtained has the following physical properties:

Melting point:63.8° C.

HCl titration:96.46%

IR cm$^{-1}$:1725, 1409

NMR δ:1.0–2.1 (10H,m), 2.1–3.4(7H,m), 4.1–4.6(2H,m).

CAPABILITY OF EXPLOITATION IN INDUSTRY

The process of the present invention makes it possible to provide, by highly safe and easy operation, high-purity 1-chlorocarbonyl-4-piperidinopiperidine or hydrochloride thereof in a high yield.

What is claimed is:

1. A process for producing 1-chlorocarbonyl-4-piperidinopiperidine hydrochloride represented by the following formula (4):

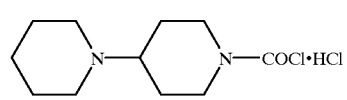

(4)

or 1-chlorocarbonyl-4-piperidinopiperidine represented by the following formula (5):

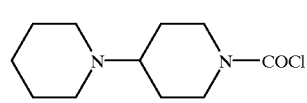

(5)

which comprises reacting 4-piperidinopiperidine represented by the following formula (1):

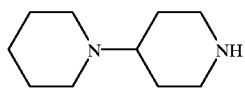

(1)

with a trialkylsilyl halide to obtain a 4-piperidinopiperidinyl trialkylsilyl represented by the following formula (2):

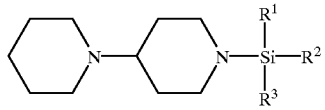

(2)

wherein $R^1$, $R^2$ and $R^3$ are the same or different and each independently represents a linear or branched $C_{1-6}$ alkyl group; reacting the resulting compound with a carbon dioxide gas to obtain a 4-piperidinopiperidinyl trialkylsilyl carbamate derivative represented by the following formula (3):

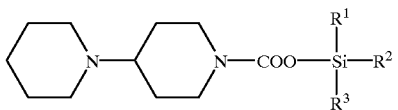

(3)

wherein $R^1$, $R^2$ and $R^3$ have the same meanings as defined above; reacting the derivative with one or more substances selected from thionyl chloride, phosphorus trichloride, phosphorus pentachloride, oxalyl chloride and phosphoryl trichloride; and optionally reacting with a strong base.

* * * * *